(12) United States Patent
Katsuki et al.

(10) Patent No.: US 12,394,526 B2
(45) Date of Patent: Aug. 19, 2025

(54) DIABETES COMPLICATION PREDICTION BY HEALTH RECORD MONITORING

(71) Applicant: INTERNATIONAL BUSINESS MACHINES CORPORATION, Armonk, NY (US)

(72) Inventors: Takayuki Katsuki, Tokyo (JP); Kohei Miyaguchi, Tokyo (JP); Akira Koseki, Yokohama (JP); Toshiya Iwamori, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 901 days.

(21) Appl. No.: 17/130,719

(22) Filed: Dec. 22, 2020

(65) Prior Publication Data

US 2022/0199260 A1   Jun. 23, 2022

(51) Int. Cl.
*G16H 50/30* (2018.01)
*G16H 10/60* (2018.01)

(52) U.S. Cl.
CPC .............. *G16H 50/30* (2018.01); *G16H 10/60* (2018.01)

(58) Field of Classification Search
None
See application file for complete search history.

(56) References Cited

U.S. PATENT DOCUMENTS 10,490,309 B1 * 11/2019 McNair ................... G16H 50/20
2008/0306434 A1 * 12/2008 Dobbles .............. A61B 5/14546
604/66

(Continued)

FOREIGN PATENT DOCUMENTS

CN   109585020 A   4/2019
CN   113192627 A   7/2021
(Continued)

OTHER PUBLICATIONS

Briggs, A., & Sculpher, M. (1998). An introduction to markov modelling for economic evaluation. PharmacoEconomics, 13(4), 397-409. doi:http://dx.doi.org/10.2165/00019053-199813040-00003 (Year: 1998).*

(Continued)

*Primary Examiner* — Emily Huynh
(74) *Attorney, Agent, or Firm* — Tutunjian & Bitetto, P.C.; Robert Richard Aragona

(57) ABSTRACT

A computer-implemented method is provided for predicting a medical event time. The method includes receiving an electronic health record (EHR) including a plurality of pairs of observation variables and corresponding timestamps. Each of the plurality of pairs include a respective observation variable and a respective corresponding timestamp. The method further includes converting the EHR into a K-dimensional vector representing a cumulative-stay time at a finite number of patient medical states, the patient medical states being determined by values of the observation variables. The method also includes processing, by a hardware processor, the K-dimensional vector using a medical event time prediction model to output a prediction of a medical event time. The medical event time prediction model has been configured through training to receive and process K-dimensional vectors converted from past EHRs to output predicted medical event times.

23 Claims, 10 Drawing Sheets

(56) References Cited

U.S. PATENT DOCUMENTS

| | | | | |
|---|---|---|---|---|
| 2012/0238853 | A1* | 9/2012 | Arefieg | G16H 40/67 |
| | | | | 600/365 |
| 2013/0116999 | A1 | 5/2013 | Stein et al. | |
| 2014/0279746 | A1* | 9/2014 | De Bruin | G16H 50/70 |
| | | | | 706/46 |
| 2017/0206327 | A1* | 7/2017 | Heywood | A61B 5/4833 |
| 2017/0319145 | A1* | 11/2017 | Pipke | G16B 5/30 |
| 2018/0144815 | A1* | 5/2018 | Chapman-McQuiston | |
| | | | | G16H 40/20 |
| 2019/0034591 | A1* | 1/2019 | Mossin | G06N 3/08 |
| 2020/0005941 | A1* | 1/2020 | Saria | G16H 50/20 |

FOREIGN PATENT DOCUMENTS

| | | | | |
|---|---|---|---|---|
| CN | 113517046 | A | 10/2021 | |
| JP | 5511077 | B2 * | 6/2014 | |
| JP | 2020-529057 | A | 10/2020 | |
| WO | WO-2020058928 | A1 * | 3/2020 | G06N 3/0454 |

OTHER PUBLICATIONS

Michael Hardy (https://math.stackexchange.com/users/11667/michael-hardy), kernel vs basis for the kernel, URL (version: May 2, 2017): https://math.stackexchange.com/q/2263025 (Year: 2017).*

Lodhi, H., Saunders, C., Shawe-Taylor, J., Cristianini, N., & Watkins, C. (2002). Text classification using string kernels. Journal of Machine Learning Research, 2(3), 419-44. doi:http://dx.doi.org/10.1162/153244302760200687 (Year: 2002).*

Global Dossier translation of JP-5511077-B2. (Year: 2014).*

Bindu Vekaria, Christopher Overton, Arkadiusz Wisniowski et al. Hospital Length of Stay For COVID-19 Patients: Data-Driven Methods for Forward Planning, Oct. 1, 2020, Preprint (Version 1) available at Research Square [https://doi.org/10.21203/rs.3.rs-56855/v1] (Year: 2020).*

Takahashi et al, "Predicting Battery Life from Usage Trajectory Patterns", IBM Research, Tokyo, ICPR Nov. 2012, pp. 1-4.

Bin Liu et al., "Early Prediction of Diabetes Complications from Electronic Health Records: A Multi-task Survival Analysis Approach", Association for the Advancement of Artificial Intelligence, www.aaai.org, Apr. 2018, pp. 1-8.

Anonymous, "Fine tuning Health-score estimation based on Surrounding-Context and Life Style", An IP.com Prior Art Database Technical Disclosure, Aug. 2016, pp. 1-4.

Simon et al., "Predicting diabetes clinical outcomes using longitudinal risk factor trajectories", https://doi.org/10.1186/s12911-019-1009-3, BMC Medical Informatics and Decision Making, Jan. 2020, pp. 1-9.

Pham et al, "Predicting healthcare trajectories from medical records: A deep learning approach", Journal of Biomedical Informatics, doi: http://dx.doi.org/10.1016/j.jbi.2017.04.001, Apr. 2017, pp. 1-35.

Mell et al. "The NIST Definition of Cloud Computing", NIST Special Publication 800-145, 2011, 7 pages.

International Search Report from PCT/IB2021/061107 dated Mar. 9, 2022, 9 pgs.

Japan Patent Office, "Notice of allowance" May 7, 2025, 03 Pages, JP Application No. 2023-536489.

* cited by examiner

Algorithm 1 Cumulative-stay Time Representation

Input: Raw observations $\{X, t\}$ and state function $s(\bullet)$
Output: Cumulative-stay time representation, CTR, $z$
1: Initialize: $z \leftarrow 0$
2: for $m = 1$ to $M$ (which can be parallelized over $m$)
3:      $s^{\{m\}} \leftarrow s(x^{\{m\}})$
4:      $d^{\{m\}} \leftarrow t^{\{m\}} - t^{\{m-1\}}$
5:      for $k = 1$ to $K$
6:          $z_k \leftarrow z_k + d^{\{m\}} s_k^{\{m\}}$

FIG. 7

DIABETES COMPLICATION PREDICTION BY HEALTH RECORD MONITORING

BACKGROUND

The present invention generally relates to Cumulative-stay Time Representations (CTR) for modeling electronic health records in prediction of diabetes and other medical health complications.

Predicting diabetes complications or some medical events from Electronic Health Records (EHRs), which represent a patient's health history, is an important task in medical and healthcare applications. For improved modeling of health history, time series in the EHR should be addressed.

SUMMARY

According to aspects of the present invention, a computer-implemented method is provided for predicting a medical event time. The method includes receiving an electronic health record (EHR) including a plurality of pairs of observation variables and corresponding timestamps. Each of the plurality of pairs include a respective observation variable and a respective corresponding timestamp. The method further includes converting the EHR into a K-dimensional vector representing a cumulative-stay time at a finite number of patient medical states, the patient medical states being determined by values of the observation variables. The method also includes processing, by a hardware processor, the K-dimensional vector using a medical event time prediction model to output a prediction of a medical event time. The medical event time prediction model has been configured through training to receive and process K-dimensional vectors converted from past EHRs to output predicted medical event times.

According to other aspects of the present invention, a computer program product is provided for predicting a medical event time. The computer program product includes a non-transitory computer readable storage medium having program instructions embodied therewith. The program instructions are executable by a computer to cause the computer to perform a method. The method includes receiving an electronic health record (EHR) including a plurality of pairs of observation variables and corresponding timestamps. Each of the plurality of pairs include a respective observation variable and a respective corresponding timestamp. The method includes converting the EHR into a K-dimensional vector representing a cumulative-stay time at a finite number of patient medical states, the patient medical states being determined by values of the observation variables. The method further includes processing the K-dimensional vector using a medical event time prediction model to output a prediction of a medical event time. The medical event time prediction model has been configured through training to receive and process K-dimensional vectors converted from past EHRs to output predicted medical event times.

According to yet other aspects of the present invention, a computer processing system is provided for predicting a medical event time. The computer processing system further includes a memory device for storing program code. The computer processing system also includes a hardware processor operatively coupled to the memory device for running the program code to receive an electronic health record (EHR) including a plurality of pairs of observation variables and corresponding timestamps. Each of the plurality of pairs include a respective observation variable and a respective corresponding timestamp. The hardware processor further runs the program code to convert the EHR into a K-dimensional vector representing a cumulative-stay time at a finite number of patient medical states, the patient medical states being determined by values of the observation variables. The hardware processor also runs the program code to process the K-dimensional vector using a medical event time prediction model to output a prediction of a medical event time. The medical event time prediction model has been configured through training to receive and process K-dimensional vectors converted from past EHRs to output predicted medical event times.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 7 is a diagram showing exemplary pseudocode for an algorithm for calculating a cumulative-stay time representation, in accordance with an embodiment of the present invention;

DETAILED DESCRIPTION

Embodiments of the present invention are directed to Cumulative-stay Time Representations (CTR) for modeling electronic health records in prediction of diabetes and other medical health complications. In particular, embodiments of the present invention can be used to predict when a patient will develop some disease after an index date from past observations in an Electronic Heath Record (HER).

For better modeling of health history, raw observations should be handled in EHR, and raw observations in each patient's EHR should be converted into a tractable representation as input for a prediction model. This is because raw observations are not structured or formatted in a way convenient for machine learning-based approaches.

The ordinary time-series representation is the common and simplest way for this purpose, and it focuses on modeling detailed dependencies between successive observations.

On the other hand, it is known that progression of some disease and complications, especially for example lifestyle and geriatric disease, are related to cumulative-stay time in specific patient's states, e.g., high blood pressure, hyperglycemia, and high fat. The ordinary time-series representation is rather inefficient for modeling the cumulative-stay time since the cumulative-stay time is an exact case of long-term dependency. Hence, it is desired to directly model/represent cumulative-stay time in specific patient's states for accurate prediction of diabetes and/or other complications.

Additionally, observation intervals may vary over time. Hence, it is desirable to handle variable observation intervals.

Thus, one or more embodiments cumulatively record the stay time for each combination of values of observation variables that represents a patient's health condition as a state. Three types of definitions are derived for the state; the first discretely determines the state assignment for observations as non-overlapping segments, and the second and third ones determine that as continuous measurements and are based on kernel functions and neural networks, respectively.

Figure 1:
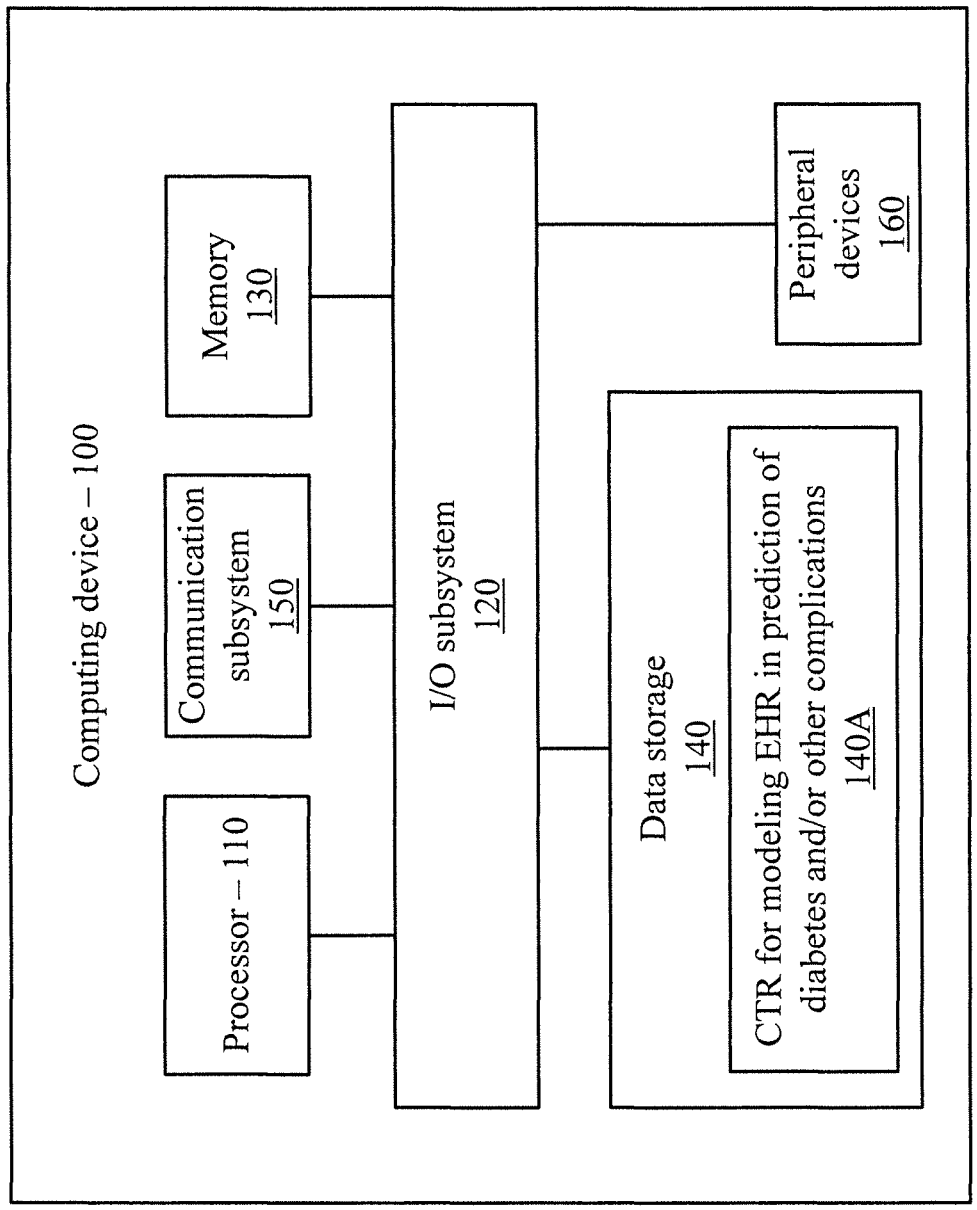
FIG. 1 is a block diagram showing an exemplary computing device, in accordance with an embodiment of the present invention.

FIG. 1 is a block diagram showing an exemplary computing device 100, in accordance with an embodiment of the present invention. The computing device 100 is configured to provide Cumulative-stay Time Representations (CTR) for modeling electronic health records in prediction of diabetes and/or other complications.

The computing device 100 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 100 may be embodied as a one or more compute sleds, memory sleds, or other racks, sleds, computing chassis, or other components of a physically disaggregated computing device. As shown in FIG. 1, the computing device 100 illustratively includes the processor 110, an input/output subsystem 120, a memory 130, a data storage device 140, and a communication subsystem 150, and/or other components and devices commonly found in a server or similar computing device. Of course, the computing device 100 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 130, or portions thereof, may be incorporated in the processor 110 in some embodiments.

The processor 110 may be embodied as any type of processor capable of performing the functions described herein. The processor 110 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 130 may be embodied as any type of volatile or non-volatile memory or data storage capable of performing the functions described herein. In operation, the memory 130 may store various data and software used during operation of the computing device 100, such as operating systems, applications, programs, libraries, and drivers. The memory 130 is communicatively coupled to the processor 110 via the I/O subsystem 120, which may be embodied as circuitry and/or components to facilitate input/output operations with the processor 110 the memory 130, and other components of the computing device 100. For example, the I/O subsystem 120 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.) and/or other components and subsystems to facilitate the input/output operations. In some embodiments, the I/O subsystem 120 may form a portion of a system-on-a-chip (SOC) and be incorporated, along with the processor 110, the memory 130, and other components of the computing device 100, on a single integrated circuit chip.

The data storage device 140 may be embodied as any type of device or devices configured for short-term or long-term storage of data such as, for example, memory devices and circuits, memory cards, hard disk drives, solid state drives, or other data storage devices. The data storage device 140 can store program code for providing Cumulative-stay Time Representations (CTR) for modeling Electronic Health Records (EHR) in prediction of diabetes and/or other complications. The communication subsystem 150 of the computing device 100 may be embodied as any network interface controller or other communication circuit, device, or collection thereof, capable of enabling communications between the computing device 100 and other remote devices over a network. The communication subsystem 150 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 100 may also include one or more peripheral devices 160. The peripheral devices 160 may include any number of additional input/output devices, interface devices, and/or other peripheral devices. For example, in some embodiments, the peripheral devices 160 may include a display, touch screen, graphics circuitry, keyboard, mouse, speaker system, microphone, network interface, and/or other input/output devices, interface devices, and/or peripheral devices.

Of course, the computing device 100 may also include other elements (not shown), as readily contemplated by one of skill in the art, as well as omit certain elements. For example, various other input devices and/or output devices can be included in computing device 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. Further, in another embodiment, a cloud configuration can be used (e.g., see FIGS. 9-10). These and other variations of the processing system 100 are readily contemplated by one of ordinary skill in the art given the teachings of the present invention provided herein.

As employed herein, the term "hardware processor subsystem" or "hardware processor" can refer to a processor, memory (including RAM, cache(s), and so forth), software (including memory management software) or combinations thereof that cooperate to perform one or more specific tasks.

In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), FPGAs, and/or PLAs.

Figure 2:
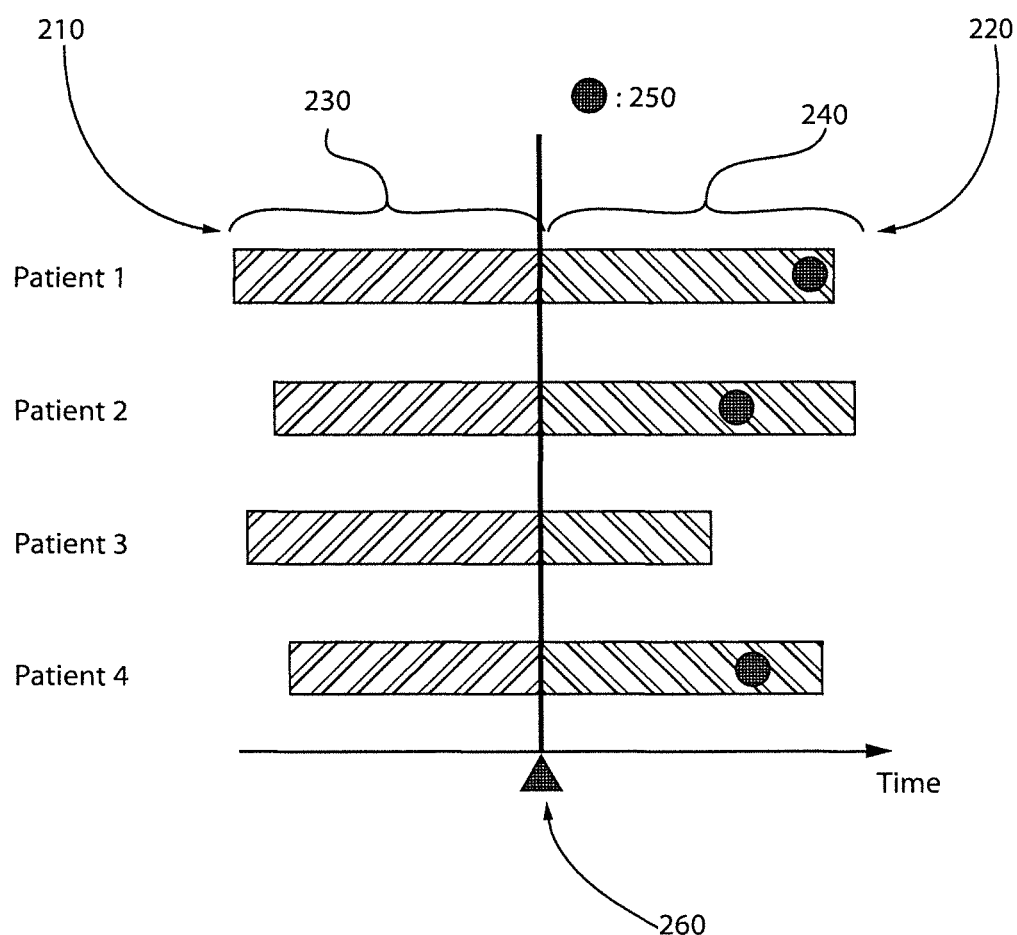
FIG. 2 is a block diagram showing an exemplary representation for raw observations as a k dimensional vector, in accordance with an embodiment of the present invention.

These and other variations of a hardware processor subsystem are also contemplated in accordance with embodiments of the present invention FIG. 2 is a block diagram showing an exemplary representation 200 for raw observations as a k dimensional vector, in accordance with an embodiment of the present invention.

The representation 200 involves patient 1 through patient 4, an initial observation time 210, a censored time 220, an observation window 230, and a prediction window 240. In the prediction windows, disease development 250 may be indicated. An index date of prediction 260 corresponds to the end of the observation window 230. That is, the past observations for each patient come from a window that spans from the initial observation time to the index date. A model is constructed that predicts an event time of disease development on the basis of observations corresponding to a patient.

Figure 3:
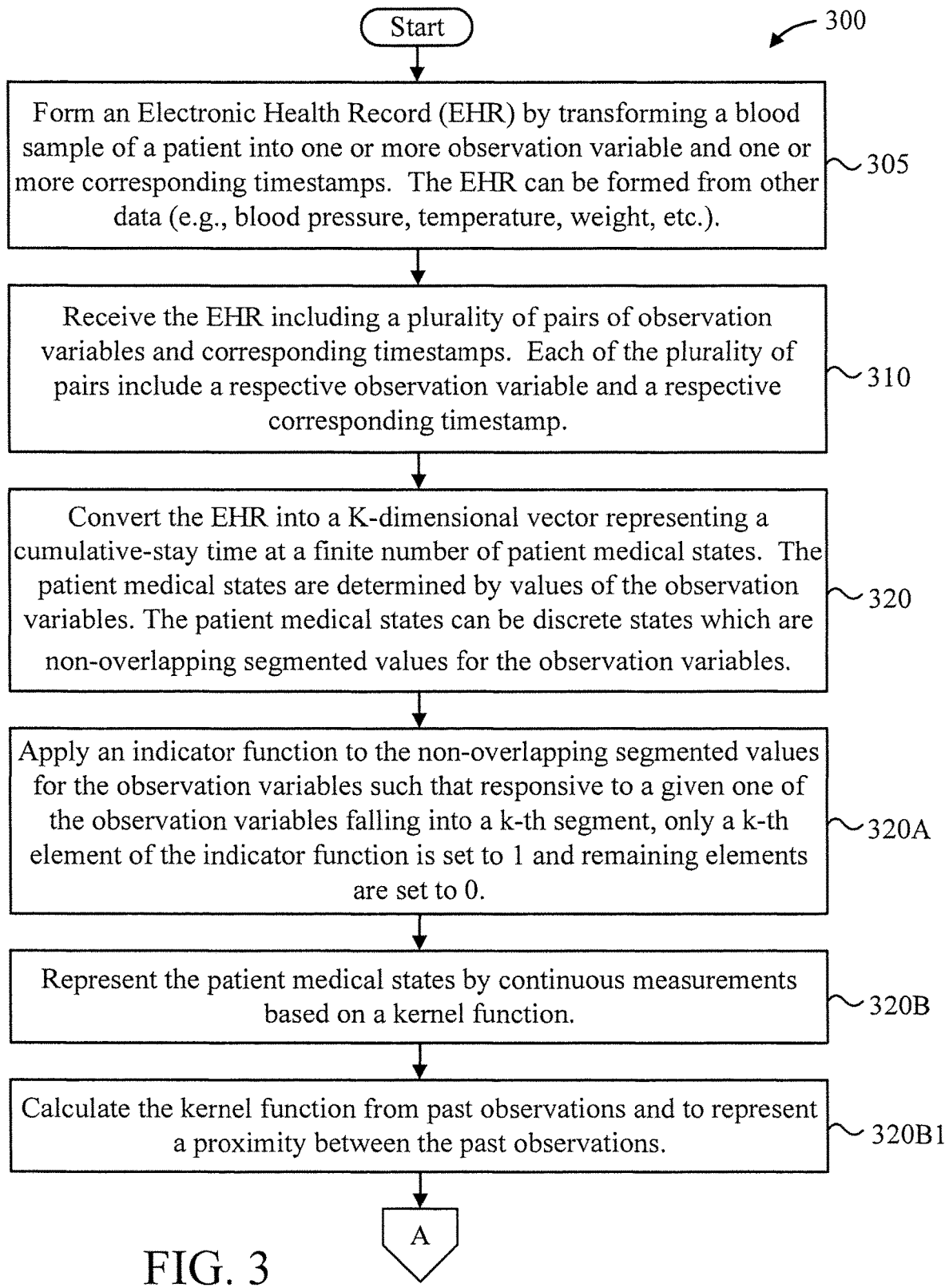
FIGS. 3-5 show an exemplary method for predicting and treating a medical event time, in accordance with an embodiment of the present invention.
Figure 4:
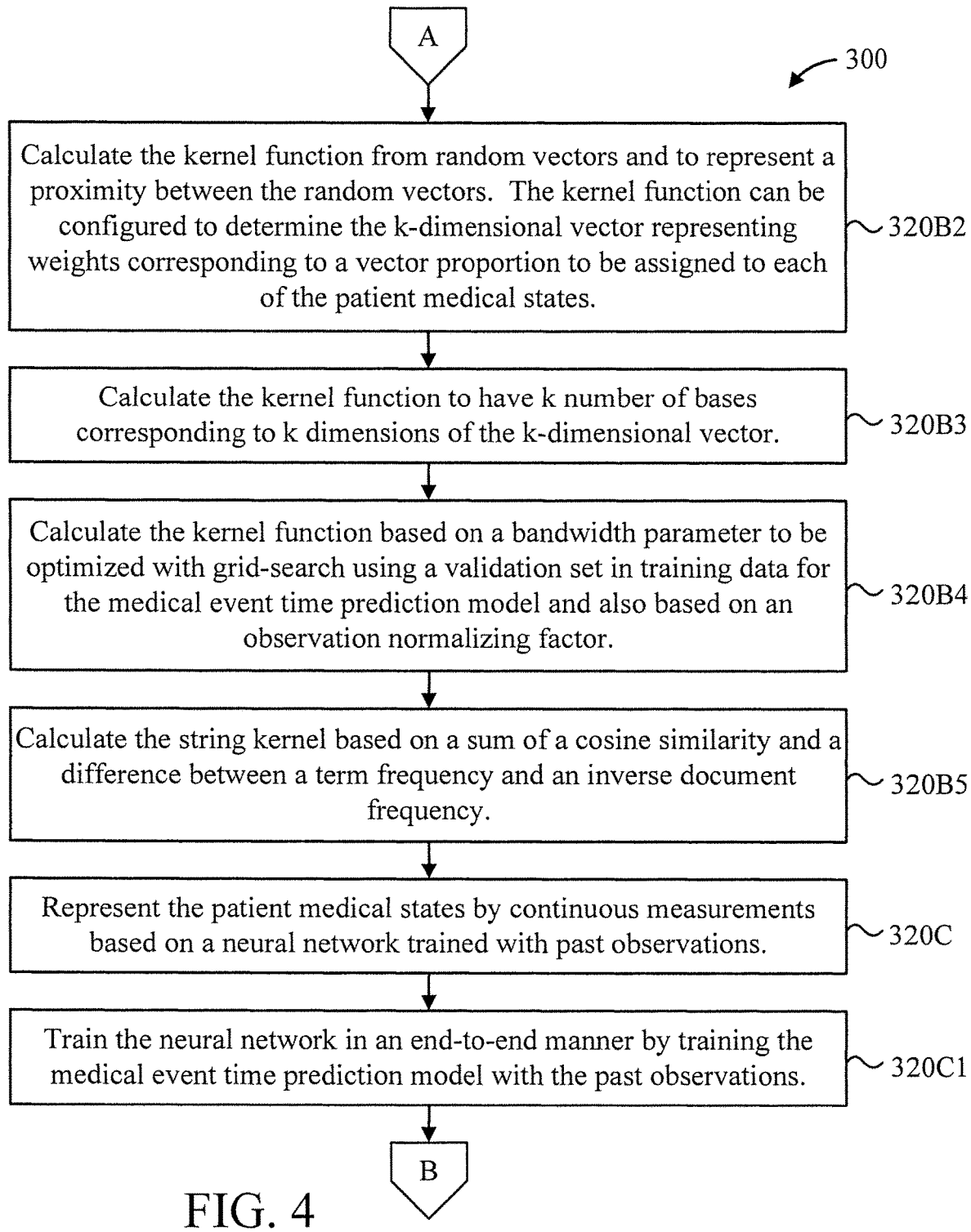
Figure 5:
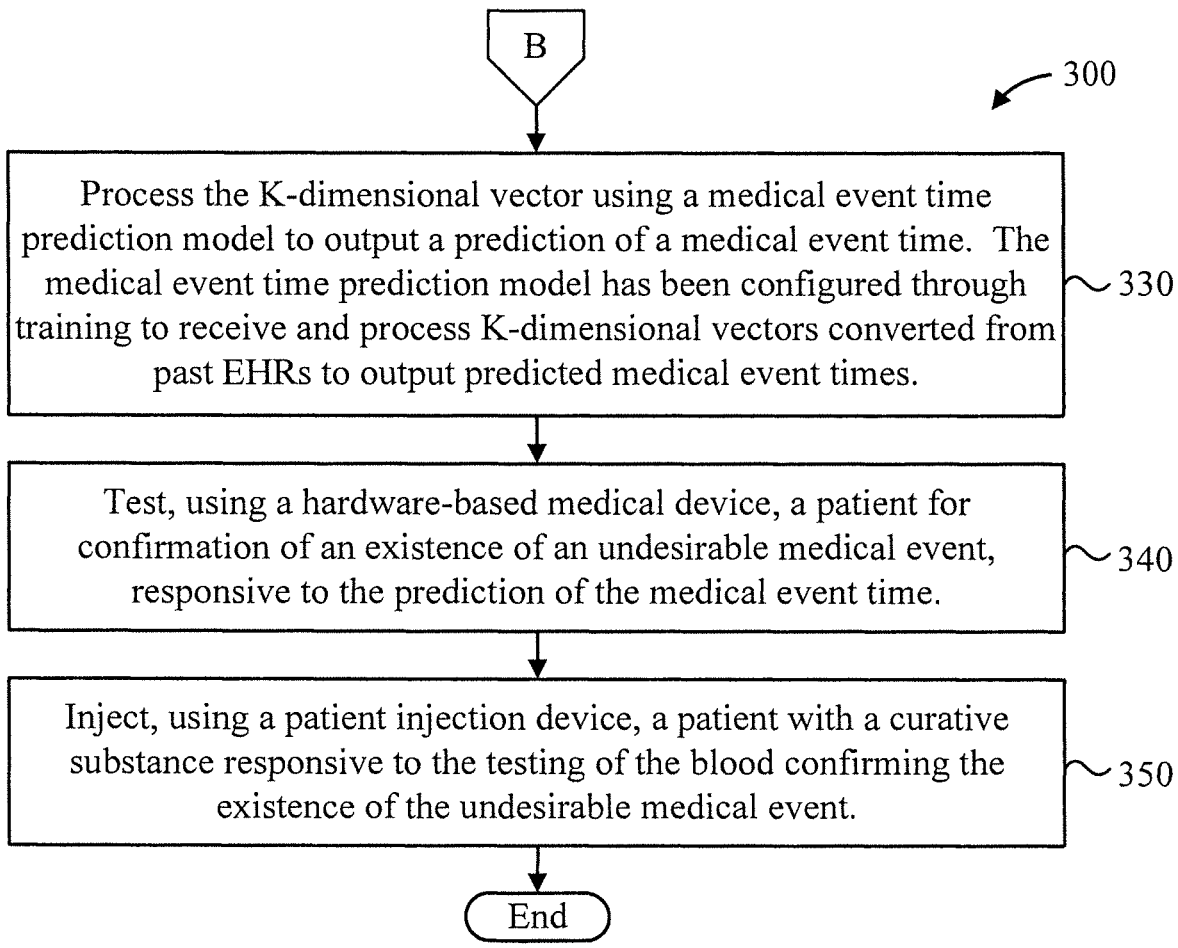

FIGS. 3-5 show an exemplary method 300 for predicting and treating a medical event time, in accordance with an embodiment of the present invention.

At block 305, form an Electronic Health Record (EHR) by transforming a blood sample of a patient into one or more observation variable and one or more corresponding timestamps. The EHR can be formed from other data (e.g., blood pressure, temperature, weight, etc.).

At block 310, receive the EHR including a plurality of pairs of observation variables and corresponding timestamps. Each of the plurality of pairs include a respective observation variable and a respective corresponding timestamp.

At block 320, convert the EHR into a K-dimensional vector representing a cumulative-stay time at a finite number of patient medical states. The patient medical states are determined by values of the observation variables. In an embodiment, the patient medical states can be discrete states which are non-overlapping segmented values for the observation variables.

In an embodiment, block 320 can include one or more of blocks 320A through 320D.

At block 320A, apply an indicator function to the non-overlapping segmented values for the observation variables such that responsive to a given one of the observation variables falling into a k-th segment, only a k-th element of the indicator function is set to 1 and remaining elements are set to 0.

At block 320B, represent the patient medical states by continuous measurements based on a kernel function.

In an embodiment, block 320B includes one or more of blocks 320B1 through 320B4.

At block 320B1, calculate the kernel function from past observations and to represent a proximity between the past observations.

At block 320B2, calculate the kernel function from random vectors and to represent a proximity between the random vectors. In an embodiment, the kernel function can be configured to determine the k-dimensional vector representing weights corresponding to a vector proportion to be assigned to each of the patient medical states.

At block 320B3, calculate the kernel function to have k number of bases corresponding to k dimensions of the k-dimensional vector.

At block 320B4, calculate the kernel function based on a bandwidth parameter to be optimized with grid-search using a validation set in training data for the medical event time prediction model and also based on an observation normalizing factor.

In an embodiment, the kernel function can include a string kernel for binary features. To that end, at block 320B5, calculate the string kernel based on a sum of a cosine similarity between a term frequency and an inverse document frequency.

At block 320C, represent the patient medical states by continuous measurements based on a neural network trained with past observations.

Block 320C can include block 320C1.

At block 320C1, train the neural network in an end-to-end manner by training the medical event time prediction model with the past observations.

At block 320D, calculate the cumulative-stay time as a sum of products of multiple k-dimensional vectors and durations staying in the patient medical states.

At block 330, process the K-dimensional vector using a medical event time prediction model to output a prediction of a medical event time. The medical event time prediction model has been configured through training to receive and process K-dimensional vectors converted from past EHRs to output predicted medical event times.

At block 340, test, using a hardware-based medical device, a patient for confirmation of an existence of an undesirable medical event, responsive to the prediction of the medical event time. For example, a diabetic complication can be detected such as high blood sugar, gout, and so forth. In an embodiment, the blood and/or vision of a patent is tested using a blood analysis device and a vision testing device, respectively. The hardware-based medical device can be a centrifuge, a needle, an automated vision test, and/or so forth.

At block 350, inject, using a patient injection device, a patient with a curative substance responsive to the testing of the blood confirming the existence of the undesirable medical event. The curative substance can be a medicine or other substance (e.g., glucose) for treating a particular condition/complication.

A description will now be given of an illustrative embodiment.

In the embodiment, raw observations and time stamps are converted into a k-dimensional vector $z \in \mathbb{R}^K$ which represents cumulative-stay time at a finite number of states. The states are determined by values of observation variables.

By using the difference between consecutive times $t_s$, $d \equiv \{d^{\{1\}}, d^{\{1\}}, \ldots, d^{\{M\}}\}$, z is defined with state function s as $z(X, t) \equiv \Sigma d^{\{m\}} s(x^{\{m\}})$.

Further to the illustrative embodiment, a description will now be given regarding state function variants, in accordance with various embodiments of the present invention.

A description will now be given regarding a state function variant implemented by discrete states.

In such a case, the state function s can be represented as follows:

$$s(x^{\{m\}}) = I(x^{\{m\}}, A)$$

where A is K number of non-overlapping collectively exhaustive value segments. The segment for the k-th state $a_k$ represents the combination of D number of the value ranges for D number of attributes in x. I is the indicator function, where if x falls into the k-th segment, only the k-th element of I becomes 1 and the others are 0.

In such a case, the discrete state can be seen as bins of non-overlapping segmented values for observation variables. Each bin is filled with the corresponding stay time of a patient.

A description will now be given regarding a state function variant implemented by continuous states using a kernel function.

In such a case, the state function $s_K$ can be represented as follows:

$$s_K(x^{\{m\}}) = \phi(x^{\{m\}}, X').$$

Since the number of the discrete state grows exponentially with the number of features D, a kernel is used with K number of bases $X' \equiv \{x'^{\{k\}}\}_{k=1}^{K}$, where $x'^{\{k\}} \in R^D$ is a k-th basis. The kernel function Φ outputs K-dimensional vector representing weights determining at what proportion the present invention assigns the current stay time to each state represented by bases. The kernel function also leads to smooth interpolation between states. Bases can be randomly sampled from training data.

A description will now be given regarding a state function variant implemented by continuous states using a neural network.

In such a case, the state function $s_N$ can be represented as follows:

$$s_N(x^{\{m\}}) = g(x^{\{m\}}, \theta_g).$$

The kernel function can be replaced with a neural network which is trained in end-to-end manner, where $\theta_\Phi$ is parameters for the neural network, where the neural network g also outputs a K-dimensional vector for representing the weight vector for states.

It is to be appreciated that k-dimensional vector z does not have a time-axis but maintains temporal information as cumulative-stay time at each state, which provides a lightweight approach representing time-series and can be parallelized over observations. In addition, it can naturally handle variable observation interval since d is directly encoded.

Note that standardization is applied to k-dimensional vector z for handling variable N which depends on each instance in the current implementation. Moreover, interpolation can be used to fix variable N.

As can be seen, the continuous states involving kernel functions and neural networks avoid exponential increases in the number of states and lead to smooth interpolation between states.

Figure 6:
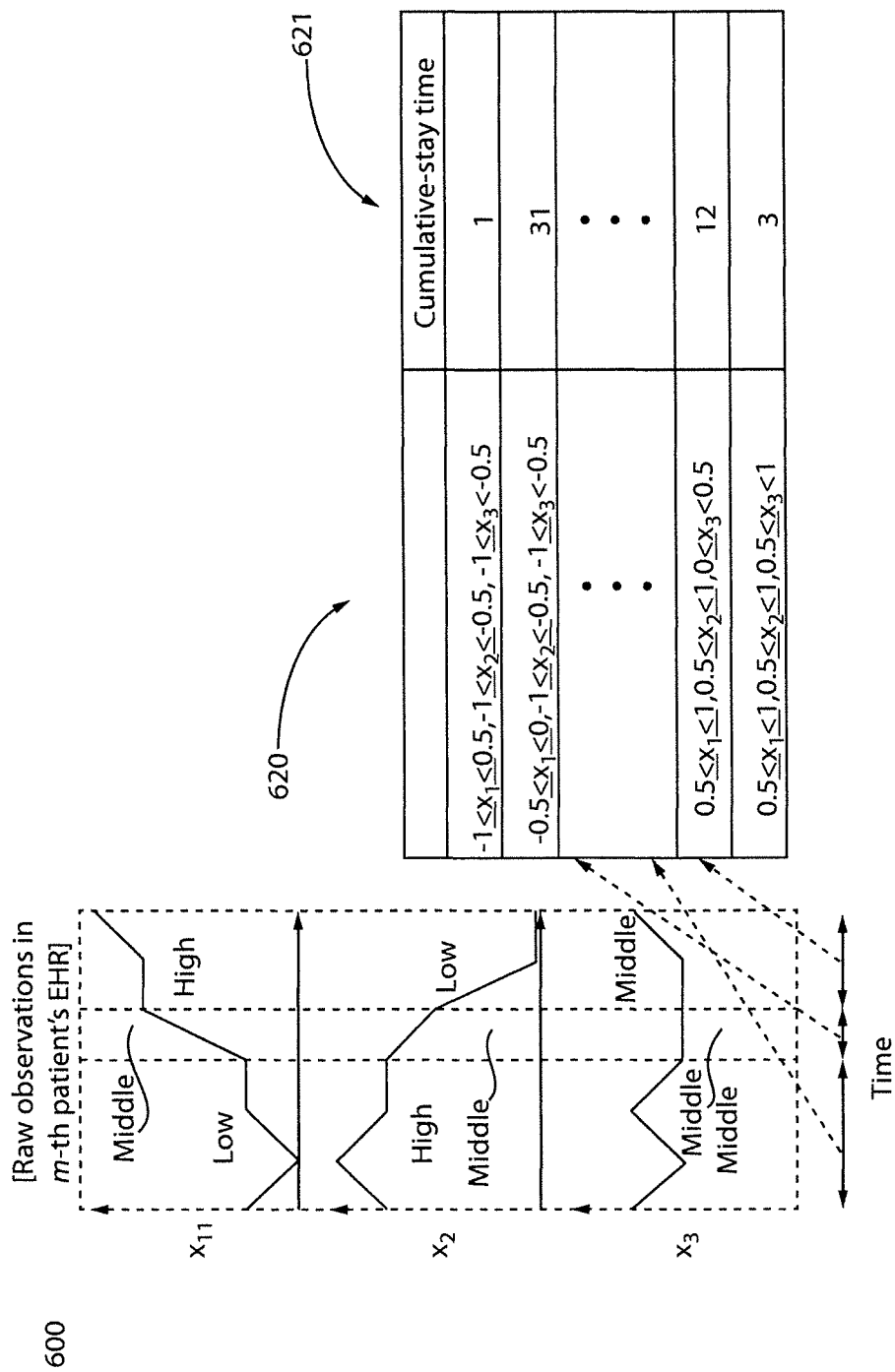
FIG. 6 is a diagram showing exemplary plots and corresponding data for cumulative-stay time representation, in accordance with an embodiment of the present invention.

FIG. 6 is a diagram showing exemplary plots 600 and corresponding data 620 for cumulative-stay time representation, in accordance with an embodiment of the present invention.

In the plots, the x-axis represents time, and the y-axis represents the values of raw observation variables in a m-th patient's EHR. As can be seen, the values of the raw observation variables span from anywhere from low to high as indicated in the plots 600.

The corresponding data, that is, the cumulative-stay time 621 for each state is calculated as shown in block 620. That is, the cumulative stay time is recorded at each combination of values of the observation variables.

FIG. 7 is a diagram showing exemplary pseudocode 700 for an algorithm for calculating a cumulative-stay time representation, in accordance with an embodiment of the present invention.

The input to the algorithm includes raw observations {X, t} and state function s.

The output from the algorithm includes a Cumulative-stay Time Representation CTR (k-dimensional vector).

A description will now be given regarding using continuous states per the kernel function, in accordance with an embodiment of the present invention.

As noted above, the state function $s_K$ can be represented as follows:

$$s_K(x^{\{m\}}) = \phi(x^{\{m\}}, X').$$

In an implementation, ϕ is a RBF kernel as follows:

$$\phi(x^{\{m\}}, X') \equiv \left\{ \frac{\exp(-\gamma \|x^{\{m\}} - x'^{\{k\}}\|^2)}{Z_m} \right\}_{k=1}^{K}$$

where y is a band width parameter to be optimized with grid-search using validation set in training data and $Z_m$ is a normalizing factor for the m-th observation.

Other kernels representing proximity between past observations can be used, such as a string kernel (e.g., tf-idf vector τ(x)+cosine similarity) for binary features as follows:

$$\phi(x^{\{n\}}, X') \equiv \left\{ \frac{\tau(x^{\{n\}}) \tau(x^{\{k\}}))}{|\tau(x^{\{n\}})||\tau(x^{\{k\}}))|} \right\}_{k=1}^{K}.$$

A description will now be given regarding using continuous states per the kernel function, in accordance with an embodiment of the present invention.

As noted above, the state function $s_N$ can be represented as follows:

$$S_N(x^{\{m\}}) = g(x^{\{m\}}, \theta_g).$$

For learning g from data, a multilayer neural network can be used for g as follows:

$$g(x^{\{m\}}, \theta_\phi) = \sigma(w_l h_{l-1}(x^{\{m\}}) + b_l).$$

where σ is an activation function, which is ReLU for the middle layers and softmax for the final output layer in an implementation, $h_{l-1}$ is outputs of l-1-th layer (previous layer), and $\theta_\phi \equiv \{w_l, b_l\}_{l-1}^{L}$ are parameters for the neural network.

A description will now be given regarding medical event time prediction from EHR, in accordance with an embodiment of the present invention.

A model is constructed for predicted an event time y>0, after an index date on the basis of past raw observations in HER, which are M numbers of pairs of observation variables and the corresponding timestamps, {X, t}. The observation variables are $X \equiv \{x^{\{m\}}\}_{m=1}^{M}$, where the m-th observation variable $x^{\{m\}}$ is represented as a D-dimensional vector $x^{\{m\}} \in \mathbb{R}^D$, and X thus forms a M×D matrix. The timestamps are $t \equiv \{t^{\{m\}}\}_{m=1}^M$, where the m-th timestamp is $t^{\{m\}} > 0$. Note that it is presumed here that observation intervals can vary over time and that the length of sequence M can be different over patients, as shown in FIG. 2.

Figure 8:
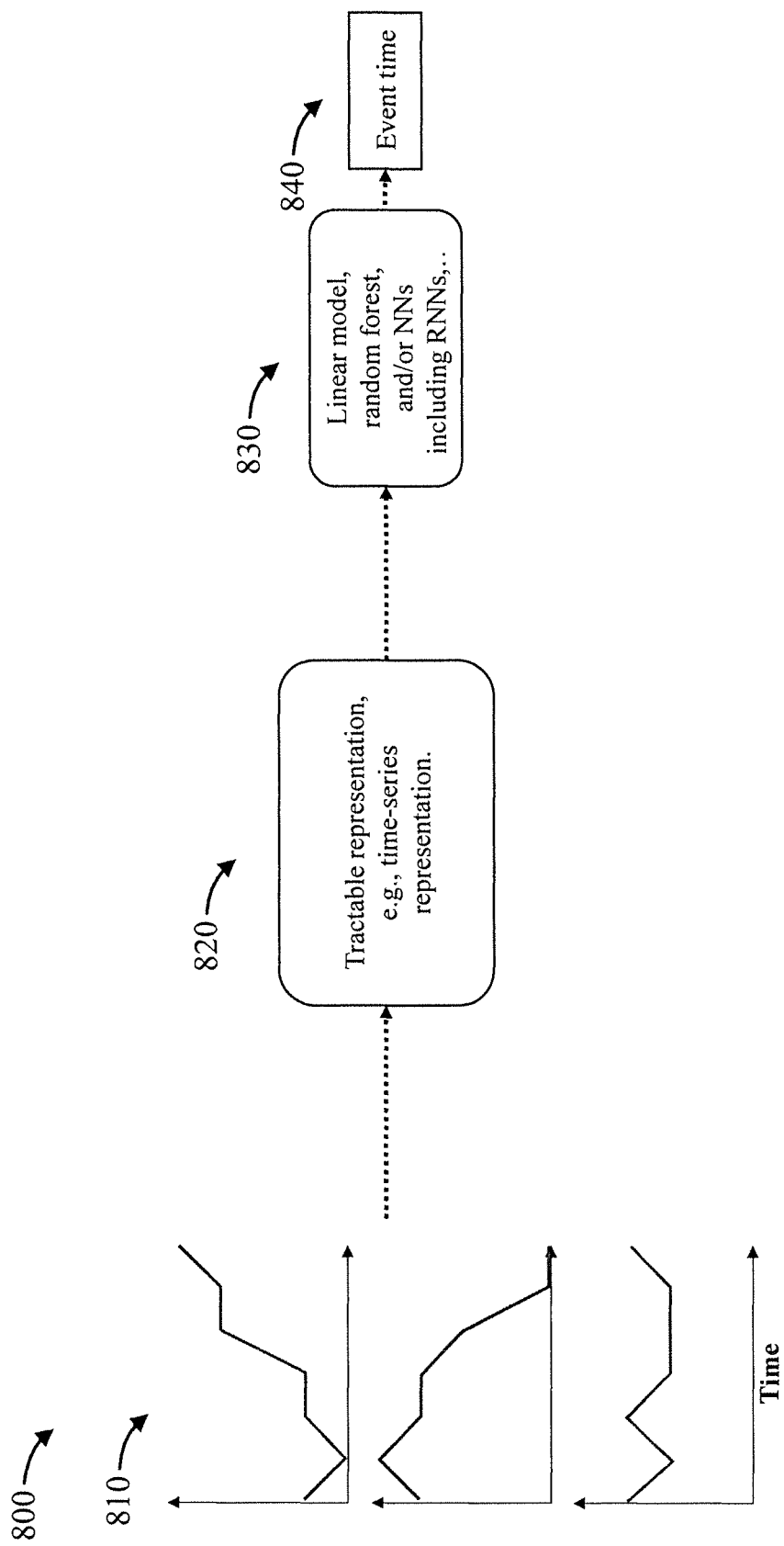
FIG. 8 is a block diagram showing an exemplary system, in accordance with an embodiment of the present invention.

When a machine learning approach is taken, the raw observations {X, t} 810 must be formalized into a tractable representation 820 as input for the subsequent prediction model 830 (e.g., linear model, random forest, and NN's including Recurrent Neural Networks) to obtain an event time 840 as shown in FIG. 8. FIG. 8 is a block diagram showing an exemplary system 800, in accordance with an embodiment of the present invention. The representation is defined as z as a function of {X, t}, z{X, t}, whose output forms either a vector, matrix, or tensor depending on the formalization.

Once {X, t} is formalized into z, then z is used as the input of the prediction model, f(x(X,t)), and learn the prediction model with the general scheme minimizing the expected loss as follows:

$$f^* \equiv \underset{f}{\mathrm{argmin}} E[\mathcal{L}(f(z(X, t)), y)], \quad (1)$$

where f* is the optimal regression function, L is the loss function, e.g., the squared error, L $(\hat{y}, y)=(\hat{y}, y)^2$, Poisson loss ($\hat{y}$−ylog $\hat{y}$), and Log-normal loss (log y−$\hat{y}$)$^2$, and E denotes the expectation over p(y, X, t). By using the learned f*, y can be predicted for new data as follows:

$$\hat{y}=f^*(z,X,t)). \quad (2)$$

A description will now be given regarding formalizing raw observations into a tractable representation, in accordance with an embodiment of the present invention.

Here, it is described how to formalize raw observations {X, t} into tractable representation z for predicting event time y. The cumulative-stay time of a specific patient's states is directly modeled with the construction of z. First, the ordinary time-series representation is considered. After that, the cumulative-stay time representation, CTR, is derived.

A description will now be given regarding an ordinary time-series representation, in accordance with an embodiment of the present invention.

In the ordinary time-series representation, raw observations {X; t} are converted into the representation of a matrix form, $z_{ts} \in R^{M \times D}$, whose two-dimensional index respectively represents timestamps and variable names. This corresponds to us directly using matrix X as $z_{ts}$ ignoring t, $z_{ts}(X, t) \equiv X$, or concatenating X and t as $z_{ts}(X, t) \equiv (X, t)$.

Note that this representation is not efficient for handling the cumulative-stay time, which is an exact case of long-term dependency, as discussed in Introduction. Even when using sophisticated RNN variants, the required learning cost is high to successively encode each observation in an entire time series into a cumulative-stay time completely from training data. Also, for handling this cumulative feature, RNNs need to memorize all observations and time stamps over a time series. This requires a large amount of memory since the states in RNNs are not static.

A description will now be given regarding CTR-D: Cumulative-stay Time Representation with Discrete States, in accordance with an embodiment of the present invention.

A Cumulative-stay Time Representation, CTR, is proposed for directly modeling the cumulative-stay time of a specific patient's states as a novel formalization of z. Raw observations (X; t) are converted into cumulative-stay times at a finite K number of states as K-dimensional vector z, whose k-th element is $z_k > 0$. Each state represents a combination of values of observation variables and can be seen as a bin segmented by a lattice that defines the value range of each observation variable in each state. Each bin is cumulatively filled with the stay time of which the raw observation falls into the corresponding value ranges.

By using the state function $s(x^{\{m\}}) \in \{0,1\}^K$, which outputs a one-hot vector representing the current state for input observation $x^{\{m\}}$, CTR z is defined as follows:

$$z(X,t) = \Sigma_m d^{\{m\}} s(x^{\{m\}}), \quad (3)$$

where $d^{\{m\}} \equiv t^{\{m\}} - t^{\{m-1\}}$, where $d^{\{m\}}$ is the duration for the m-th observation, which is estimated by calculating the difference between consecutive timestamps $t^{\{m\}}$ and $t^{\{m-1\}}$. Since the output of the function $s(x^{\{m\}})$ is a one-hot vector, only one element in the vector can become 1, and the others are 0, and the index for the element with value 1 represents the current state of the patient. Thus, for the m-th observation, the element of $d^{\{m\}} s(x^{\{m\}})$ with the current state becomes $d^{\{m\}}$, and the others are 0. Through the summation of $d^{\{m\}} s(x^{\{m\}})$ over m, each element of z represents the sum of durations of staying in a state over the observations. The algorithm is described in Algorithm 1. Note that this representation can explicitly handle variable observation intervals without any additional encoding, as shown in Equation (3). Also, Equation (3) does not have any recurrent computation, which allows for a reduction in the memory cost extensively compared with RNNs and to use parallel computation over the observations, which generally cannot be done with RNNs.

The state function $s(x^{\{m\}})$ is defined by the indication function I, which always outputs a K-dimensional one-hot vector:

$$s(x^{\{m\}}) = I(x^{\{m\}}, A) \quad (4)$$

where $A \in \{a_k\}_{k=1}^K$ is the K number of non-overlapping collectively exhaustive value segments. The segment for the k-th state $a_k$ represents the combination of D number of the value ranges for D number of attributes in $x^{\{m\}}$ as $a_k \equiv \{[\leftarrow_{d,k}, \xi_{d,k})\}_{d=1}^D$, where $\leftarrow_{d,k}$ and $\xi^{d,k}$ respectively represent lower and higher boundaries for d-th attribute $x_d^{\{m\}}$. Example segmentation $a_k$ is shown in the table of corresponding data 520 FIG. 5. By using $\leftarrow_{d,k}$ and $\xi_{d,k}$, the k-the element of the function I is $$[Ix^{\{m\}}, A)]_k = \Pi_d \mathbb{1}(\leftarrow_{d,k} \leq x_k^{\{m\}} < \xi_{d,k}) \quad (5)$$

where 1 (·) is the indication function which only return 1 value when the condition·satisfies and otherwise return 0. If $x^{\{m\}}$ 1 falls into the k-th segment, only the k-th element of $I(x^{\{m\}}, A)$ becomes 1 and the others are 0, because of the non-overlapping segmentation.

CTR in Equation (3) with the state function in Equation (4) is called the Cumulative-stay Time Representation with Discrete states (CTR-D). The discretely defined state $s(x^{\{m\}})$ is easy to understand. When the number of variables in x is small, the function $s(x^{\{m\}})$ in Equation (3) can be used for computing z.

However, since the number of collectively exhaustive combinations representing states grows exponentially with the number of observation variables D, it cannot handle more than several numbers of variables. States are not essentially simple enough to be modeled with such lower dimensional space in the case of EHR modeling. Also, the non-continuous boundary prevents generalization between adjacent states, though adjacent states should represent states similar to each other because of the shared boundaries between them as in the definition in Equation (4). The function $s(x^{\{m\}})$ is extended into a more practical one.

A description will now be given regarding CTR-K: Cumulative-stay Time Representation (CTR) with continuous states based on a kernel function, in accordance with an embodiment of the present invention.

For mitigating the exponential growth in the number of states, the definition of states is changed from discrete, what variable values an observation has, to continuous, how close an observation is with some basis vectors. Continuous states are no longer represented as a one-hot vector corresponding to a unique state. They are represented as a weight vector determining at what proportion the present invention assigns the current stay time to each state represented by bases. In this case, the number of the states is limited to the number of bases. This also leads to interpolation between states and can smoothly represent intermediate states between the states.

For computing the continuous state, a kernel function is used that represents affinities to bases for observations, where a continuous-valued vector is constructed by assigning different values in multiple elements according to the affinities. The state function $s_K(x^{\{m\}}) \in R^K$ based on the kernel function $\phi$ is defined as $$s_K(x^{\{m\}}) \equiv \phi(x^{\{m\}}, X') \tag{6}$$

where $X' \equiv \{x'^{\{k\}}\}_{k=1}^{K}$ is the K number of bases, and $x'^{\{k\}} \in R^D$ is the k-th basis. For example, $s_K(x^{\{m\}}) = \{0, 0.3, 0.7, 0, \ldots, 0\}$ means that it is assigned the stay time for the m-th observation with weights of 0.3 and 0.7 to the second and third states, respectively, in the summation in Equation (3).

When the variables are real-valued, which also includes the exemplary scenario, the choice of $\phi$ is an RBF kernel defined as $$\phi(x^{\{m\}}, X') = \left\{ \frac{\exp(-\gamma \|x^{\{m\}} - x'^{\{k\}}\|^2)}{Z_m} \right\}_{k=1}^{K} \tag{7}$$

where $\gamma$ is a bandwidth parameter to be optimized with a grid-search using training data, and $Z_m \equiv \Sigma_k \exp(-0.5\gamma/|x^{\{m\}} - x'^{\{k\}}/|^2)$ is a normalizing factor for the m-th observation, which comes from the requirement for using $S_K$ as weights for assigning the stay time in Equation (3). Other kernels can also be used, such as a string kernel, e.g., tf-idf vector+cosine similarity, for binary features.

CTR in Equation (3) is called with the state function in Eq. (6) the cumulative-stay time representation with kernel-defined 266 states (CTR-K).

A description will now be given regarding CTR-N: Cumulative-stay Time Representation (CTR) with continuous states based on a neural network, in accordance with an embodiment of the present invention.

Additionally, it can be seen that the requirement for continuous state $s_K(x_{\{m\}})$ in Equation (6) is to represent a similar observation with a similar weight vector. Such a vector can also be modeled with neural networks.

Thus, $s_K(x^{\{m\}})$ is extended to $s_N(x^{\{m\}})$ by replacing the kernel function with a trainable neural network, g, that produces a state-indicating weight vector similar to $\phi$, as $$s_N(x^{\{m\}}) \equiv g(x^{\{m\}}, \theta_g) \tag{8}$$

where $\theta_g$ are parameters for the neural network. The final layer for g is a softmax function for normalization as a weight vector. The specific neural network structure for g is shown in the Experimental Results section.

CTR in Equation (3) with the state function in Equation (8) is called the cumulative-stay time representation with neural network-defined states (CTR-N). This representation can be learned from data and thus provides more flexibility in adjusting the state definition to target data.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
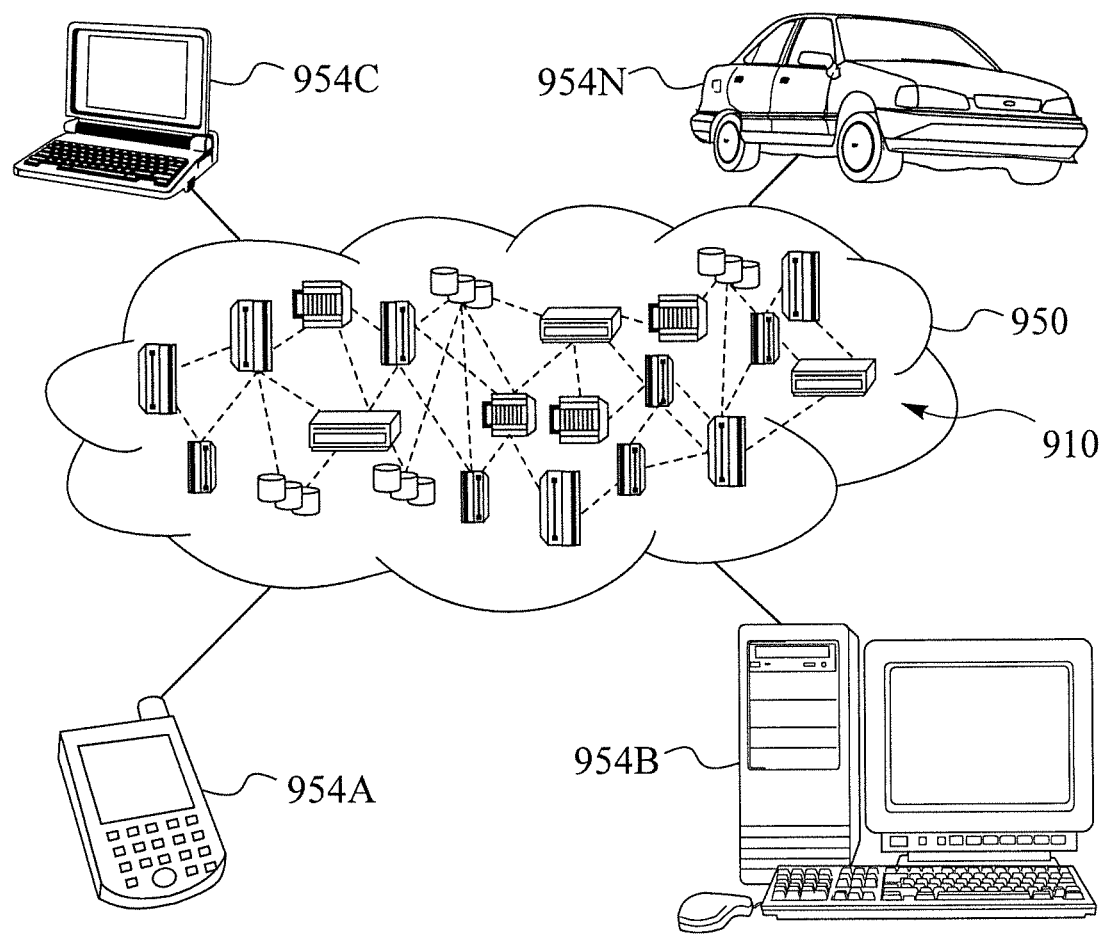
FIG. 9 is a block diagram showing an illustrative cloud computing environment having one or more cloud computing nodes with which local computing devices used by cloud consumers communicate, in accordance with an embodiment of the present invention.

Referring now to FIG. 9, illustrative cloud computing environment 950 is depicted. As shown, cloud computing environment 950 includes one or more cloud computing nodes 910 with which local computing devices used by cloud consumers, such as, for example, personal digital assistant (PDA) or cellular telephone 954A, desktop computer 954B, laptop computer 954C, and/or automobile computer system 954N may communicate. Nodes 910 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 910 and cloud computing environment 950 can communicate with any type of computerized device over any type of network and/or network addressable connection (e.g., using a web browser).

Figure 10:
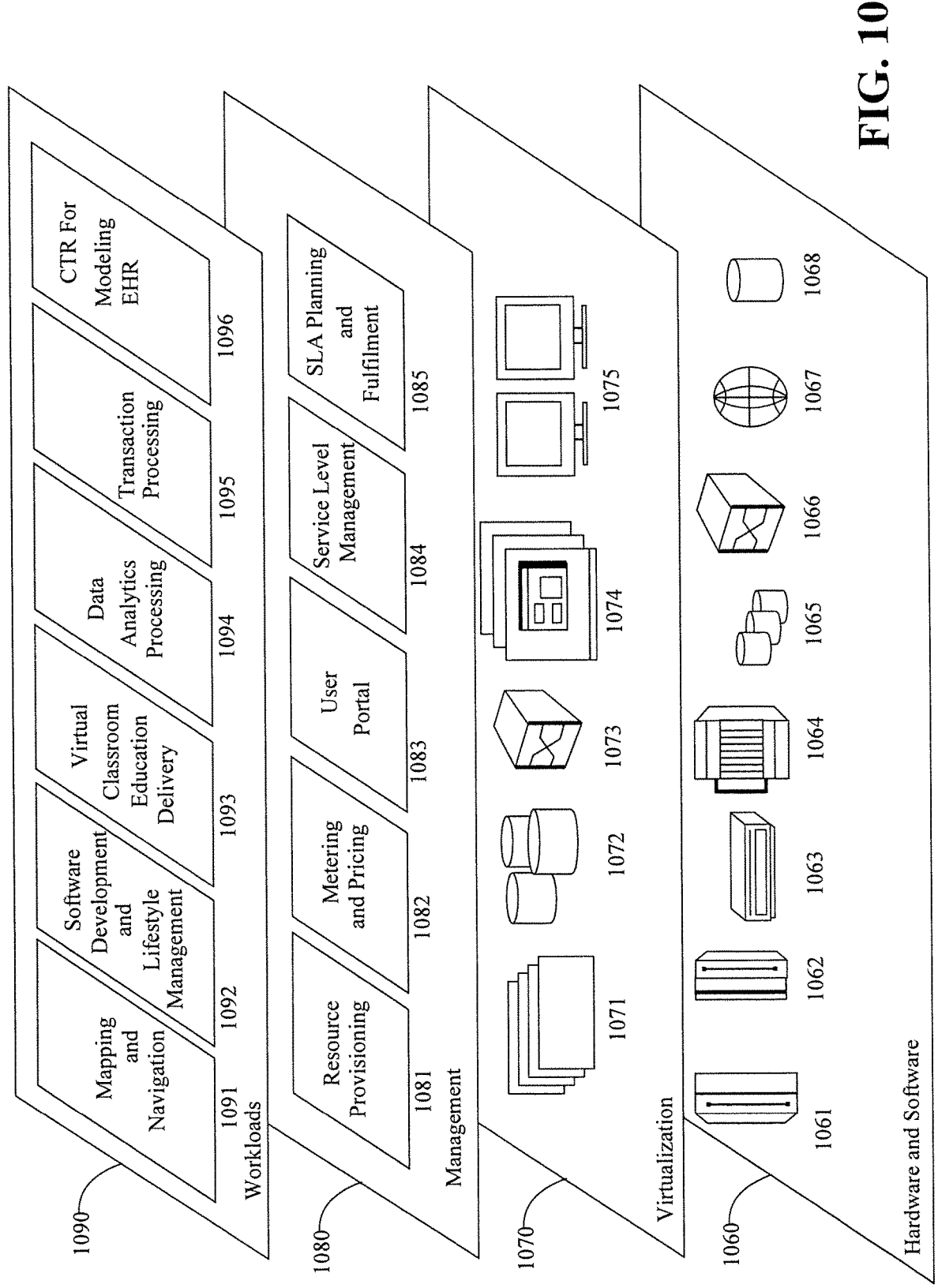
FIG. 10 is a block diagram showing a set of functional abstraction layers provided by a cloud computing environment, in accordance with an embodiment of the present invention.

Referring now to FIG. 10, a set of functional abstraction layers provided by cloud computing environment 950 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 1060 includes hardware and software components. Examples of hardware components include: mainframes 1061; RISC (Reduced Instruction Set Computer) architecture based servers 1062; servers 1063; blade servers 1064; storage devices 1065; and networks and networking components 1066. In some embodiments, software components include network application server software 1067 and database software 1068.

Virtualization layer 1070 provides an abstraction layer from which the following examples of virtual entities may be provided: virtual servers 1071; virtual storage 1072; virtual networks 1073, including virtual private networks; virtual applications and operating systems 1074; and virtual clients 1075.

In one example, management layer 1080 may provide the functions described below. Resource provisioning 1081 provides dynamic procurement of computing resources and other resources that are utilized to perform tasks within the cloud computing environment. Metering and Pricing 1082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1083 provides access to the cloud computing environment for consumers and system administrators. Service level management 1084 provides cloud computing resource allocation and management such that required service levels are met. Service Level Agreement (SLA) planning and fulfillment 1085 provide pre-arrangement for, and procurement of, cloud computing resources for which a future requirement is anticipated in accordance with an SLA.

Workloads layer 1090 provides examples of functionality for which the cloud computing environment may be utilized. Examples of workloads and functions which may be provided from this layer include: mapping and navigation 1091; software development and lifecycle management 1092; virtual classroom education delivery 1093; data analytics processing 1094; transaction processing 1095; and CTR for modeling EHR in prediction of diabetes and other medical health complications 1096.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and second listed options (A and B) only, or the selection of the first and third listed options (A and C) only, or the selection of the second and third listed options (B and C)

only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A computer-implemented method for predicting a medical event time, the method comprising:
receiving an electronic health record (EHR) including a plurality of pairs of observation variables and corresponding timestamps, wherein each of the plurality of pairs include a respective observation variable and a respective corresponding timestamp;
converting the EHR into a K-dimensional vector representing a cumulative-stay time at a finite number of patient medical states, by determining differences between patient medical states for different observation times, the patient medical states being determined by a combination of values of the observation variables;
processing, by a processor device, the K-dimensional vector using a medical event time prediction model, including a recurrent neural network, wherein the medical event time prediction model has been configured through training to receive and process K-dimensional vectors converted from past EHRs to obtain a function of the patient medical states;
predicting a medical event time of an undesirable medical event using the medical event time prediction model based on the function of the patient medical states;
communicate, through a network, cumulative-stay time representations that model a progression of patient health history including the medical event time of the undesirable medical event to computing nodes used by a patient;
generating program instructions to test, using a hardware based medical device, a blood of a patient for confirmation of an existence of the undesirable medical event, responsive to the prediction of the medical event time; and
generating program instructions to inject, using a patient injection device, a patient with a curative substance that regulates blood sugar levels of the patient responsive to the testing of the blood confirming the existence of diabetes as the undesirable medical event.

2. The computer-implemented method of claim 1, wherein the cumulative-stay time is calculated as a sum of products of multiple K-dimensional vectors and durations staying in the patient medical states.

3. The computer-implemented method of claim 1, wherein the patient medical states are discrete states which are non-overlapping segmented values for the observation variables.

4. The computer-implemented method of claim 3, further comprising applying an indicator function to the non-overlapping segmented values for the observation variables such that responsive to a given one of the observation variables falling into a k-th segment, only a k-th element of the indicator function is set to 1 and remaining elements are set to 0.

5. The computer-implemented method of claim 1, wherein the patient medical states are represented by continuous measurements based on a kernel function.

6. The computer-implemented method of claim 5, wherein the kernel function is calculated from past observations and represents a proximity between the past observations.

7. The computer-implemented method of claim 5, wherein the kernel function is calculated from random vectors and represents a proximity between the random vectors.

8. The computer-implemented method of claim 5, wherein the kernel function determines the k-dimensional vector representing weights corresponding to a vector proportion to be assigned to each of the patient medical states.

9. The computer-implemented method of claim 5, wherein the kernel function has k number of bases corresponding to k dimensions of the k-dimensional vector.

10. The computer-implemented method of claim 5, wherein the kernel function is calculated based on a bandwidth parameter to be optimized with grid-search using a validation set in training data for the medical event time prediction model and also based on an observation normalizing factor.

11. The computer-implemented method of claim 5, wherein the kernel function comprises a string kernel for binary features, wherein the string kernel is calculated based on a sum of a cosine similarity between a term frequency and an inverse document frequency.

12. The computer-implemented method of claim 1, wherein the patient medical states are represented by continuous measurements based on the recurrent neural network trained with past observations.

13. The computer-implemented method of claim 12, wherein the recurrent neural network is trained in an end-to-end manner by training the medical event time prediction model with the past observations.

14. The computer-implemented method of claim 1, further comprising parallel encoding a plurality of k-dimensional vectors over the observation variables.

15. The computer-implemented method of claim 1, further comprising forming an electronic health record by transforming a blood sample of a patient into one or more observation variables and one or more corresponding timestamps.

16. The computer-implemented method of claim 1, wherein the medical states are selected from the group consisting of high blood pressure above a given amount threshold past a given time threshold, hyperglycemia above a given amount threshold past a given time threshold, and high body fat above a given amount threshold past a given time threshold.

17. A computer program product for predicting a medical event time, the computer program product comprising a non-transitory computer read able storage medium having program instructions embodied therewith, the program instructions executable by a computer to cause the computer to perform a method comprising:
receiving an electronic health record (EHR) including a plurality of pairs of observation variables and corresponding timestamps, wherein each of the plurality of pairs include a respective observation variable and a respective corresponding timestamp;

converting the EHR into a K-dimensional vector representing a cumulative-stay time at a finite number of patient medical states, by determining differences between patient medical states for different observation times, the patient medical states being determined by a combination of values of the observation variables;

processing the K-dimensional vector using a medical event time prediction model, including a recurrent neural network, wherein the medical event time prediction model has been configured through training to receive and process K-dimensional vectors converted from past EHRs to obtain a function of the patient medical states;

predicting a medical event time of an undesirable medical event using the medical event time prediction model based on the function of the patient medical states;

communicating, through a network, cumulative-stay time representations that model a progression of patient health history including the medical event time of the undesirable medical event to computing nodes used by a patient;

testing, using a hardware based medical device, a blood of a patient for confirmation of an existence of the undesirable medical event, responsive to the prediction of the medical event time; and injecting, using a patient injection device, a patient with a curative substance that regulates blood sugar levels of the patient responsive to the testing of the blood confirming the existence of diabetes as the undesirable medical event.

18. The computer program product of claim 17, wherein the patient medical states are discrete states which are non-overlapping segmented values for the observation variables.

19. The computer program product of claim 17, wherein the patient medical states are represented by continuous measurements based on a kernel function.

20. The computer program product of claim 19, wherein the kernel function is calculated from past observations and represents a proximity between the past observations.

21. The computer program product of claim 19, wherein the kernel function is calculated from random vectors and represents a proximity between the random vectors.

22. The computer program product of claim 17, wherein the patient medical states are represented by continuous measurements based on a neural network trained with past observations.

23. A computer processing system for predicting a medical event time, comprising:
a memory device for storing program code; and
a processor device operatively coupled to the memory device for running the program code to:
receive an electronic health record (EHR) including a plurality of pairs of observation variables and corresponding timestamps, wherein each of the plurality of pairs include a respective observation variable and a respective corresponding timestamp;
convert the EHR into a K-dimensional vector representing a cumulative-stay time at a finite number of patient medical states, by determining differences between patient medical states for different observation times, the patient medical states being determined by a combination of values of the observation variables;
process, by a processor device, the K-dimensional vector using a medical event time prediction model, including a recurrent neural network, wherein the medical event time prediction model has been configured through training to receive and process K-dimensional vectors converted from past EHRs to obtain a function of the patient medical states;
predict a medical event time of an undesirable medical event using the medical event time prediction model based on the function of the patient medical states;
communicate, through a network, cumulative-stay time representations that model a progression of patient health history including the medical event time of the undesirable medical event to computing nodes used by a patient;
test, using a hardware based medical device, a blood of a patient for confirmation of an existence of the undesirable medical event, responsive to the prediction of the medical event time; and
inject, using a patient injection device, a patient with a curative substance that regulates blood sugar levels of the patient responsive to the testing of the blood confirming the existence of diabetes as the undesirable medical event.

* * * * *